United States Patent [19]
Hartmann et al.

[11] Patent Number: 4,744,131
[45] Date of Patent: May 17, 1988

[54] APPARATUS FOR HANDLING FISH FILLETS FOR THE PURPOSE OF QUALITY INSPECTION

[75] Inventors: Franz Hartmann, Bad Oldesloe; Klaus Matern, Lübeck, both of Fed. Rep. of Germany

[73] Assignee: Nordischer Maschinenbau Rud. Baader GmbH+C KG, Lubeck, Fed. Rep. of Germany

[21] Appl. No.: 106,857

[22] Filed: Oct. 8, 1987

Related U.S. Application Data

[62] Division of Ser. No. 881,119, Jul. 2, 1986, Pat. No. 4,706,336.

[51] Int. Cl.⁴ .............................................. A22C 25/00
[52] U.S. Cl. ............................................ 17/55; 17/54
[58] Field of Search ...................... 17/1 R, 54, 53, 45, 17/24, 55

[56] References Cited

U.S. PATENT DOCUMENTS

| | | | |
|---|---|---|---|
| 3,800,363 | 4/1974 | Lapeyre | 17/54 X |
| 4,557,014 | 12/1985 | Vogt | 17/1 R |
| 4,557,019 | 12/1985 | Van Devanter et al. | 17/54 X |

FOREIGN PATENT DOCUMENTS 0961631 9/1982 U.S.S.R. .................................. 17/54

Primary Examiner—Willie G. Abercrombie
Attorney, Agent, or Firm—Thomas R. Morrison

[57] ABSTRACT

The invention concerns an apparatus which can be utilized for the quality inspection of fish fillets and enables the detection of faulty spots resulting from processing deficiencies, such as skin or fin remainders, blood spots, bones, as well as from parasites and others. To this end, fillets are guided to a light emitter by means of a conveyor belt which is made from a material which allows light to pass at low absorption. The light emitter comprises light sources which are arranged out of direct sight by means of screens. Due to its characteristic to allow light to pass by dispersion, the fillet will appear illuminated in darker surroundings.

19 Claims, 1 Drawing Sheet

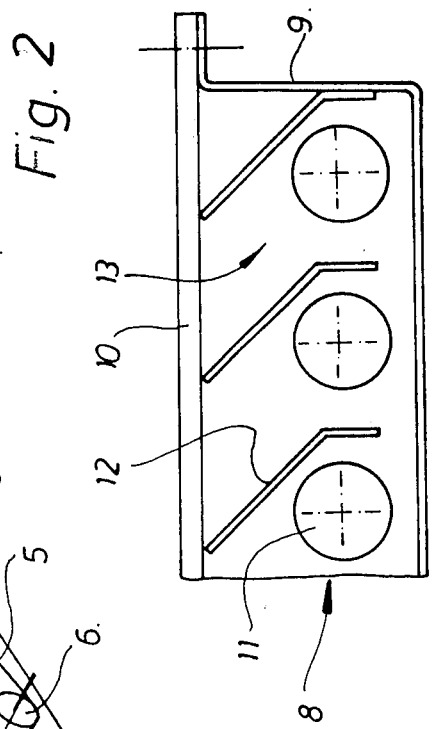
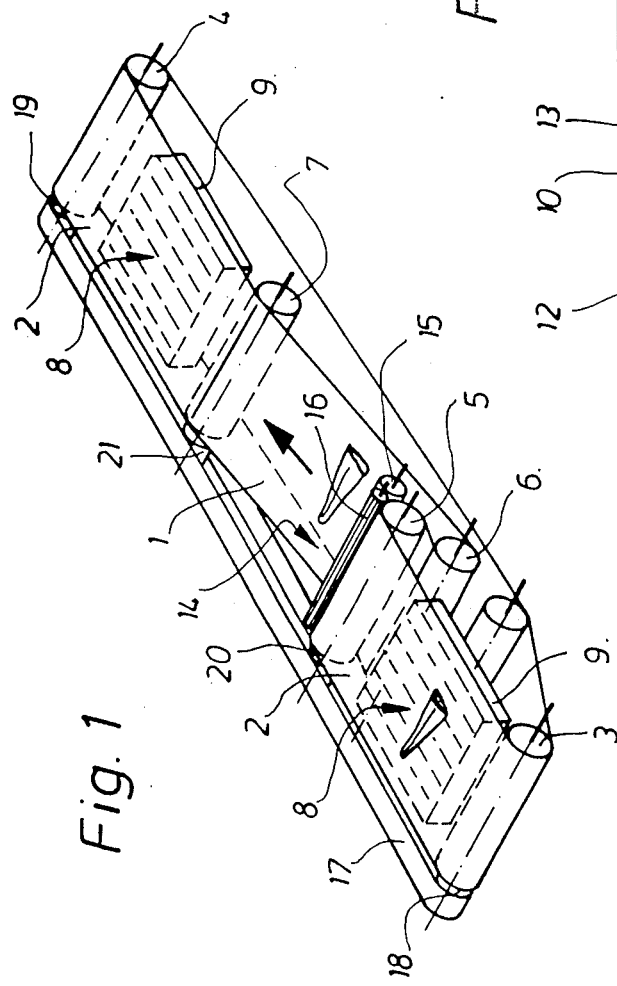

APPARATUS FOR HANDLING FISH FILLETS FOR THE PURPOSE OF QUALITY INSPECTION

This application is a division of application Ser. No. 881,119, filed July 2, 1986, now U.S. Pat. No. 4,706,336, issued 11/17/87.

BACKGROUND OF THE INVENTION

1. Field of the Invention

The invention concerns an apparatus for handling fillets of fish for the purpose of detecting and monitoring processing faults and deficiencies and/or parasites (nematodes) by visual inspection and checking, the apparatus comprising a light transparent depositing and supporting surface and at least one light emitter arranged below that surface.

2. Prior Art

In designing and constructing devices and arrangements for being used in quality control, testing and inspection, it is of essential importance that an early tiring of the personnel carrying out such quality control functions be avoided in order to maintain the necessary attention of such persons over a comparatively long working period. It has to be taken into account that the sensitivity and the distinguishing ability of the human eye is restricted strongly if details are to be observed in or on objects which are positioned in front of a bright background. The tendency of the eye to make up for such deficiency and match it leads to quick tiring. A device which takes these facts of quality inspection into account has been described in a German report published in AFZ in May 1985.

This publication discloses an apparatus having a glass plate as a depositing and supporting surface, below which a light source generating a light streak is moved in a manner that the light streak or stripe is conducted continuously over the total supporting surface. The movement of the light streak, as well as its brightness, can be controlled.

The effect and output which can be achieved with this apparatus can, however, not be regarded as satisfactory. The main reason for this is that the positioning of the fillet to be distinguished or discriminated and/or the positioning of light streak are comparatively very time consuming. This is particularly disadvantageous when fillets have to be inspected from both of their sides, i.e. from the meat side as well as from the skin side as is necessary for securely and accurately detecting any faults. Moreover, it is disadvantageous that by using a light streak, it cannot be prevented that the contour of the fillet at least partially appears in a bright surrounding field.

3. Objects of the Invention

It is therefore an essential object of the present invention to suggest an apparatus appropriate for a quick and accurate quality control, particularly of fish fillets. It is a further important object of the invention to suggest an apparatus which enables an uninterrupted and continuous detection of quality deficiencies from both sides of a fillet. It is yet another object of the invention to enable such detection with minimum physical stress for the persons carrying out such work.

SUMMARY OF THE INVENTION

In a fillet quality inspection apparatus comprising a light transparent depositing and supporting surface for the fillets and at least one light emitter arranged therebelow, these objects are achieved according to the present invention in that the supporting surface is designed as a driven conveyor belt rotating endlessly about at least two deflection rollers and manufactured from a material of low light absorption, that the light emitter comprises at least one tube-shaped light source emitting cold light, and that a screen is associated to the light source such that the latter is out of direct sight for a person standing beside the conveyor belt. The main advantages to be achieved thereby particularly reside in that the apparatus may form the last processing station of an automatic filleting line and can be linked thereto directly, the fillets passing the inspecting person continuously and appearing illuminated in a darker surrounding field. In a preferred embodiment the light emitter may be arranged in a hermetically sealed housing whose closing surface facing the conveyor belt has been made from a transparent material.

In order to keep the basic brightness of the supporting surface at a minimum level, the screen may preferably be designed to have a reflecting surface on its side facing the light source and a light absorbing surface on its side remote of the light source. According to another preferred embodiment the conveyor belt may be provided with a fillet turning station intermediate between the two deflection or reversing rollers, which turning station serves to turn the fillets lying on their skin side onto their meat side. This enables an automatic transferring of the fillets to a second apparatus, also having the structure of the present invention, which may follow or be connected to the turning station, which second apparatus will enable an inspection of the fillets from their skin side. The structure of the turning station can be such that it comprises a turning roller rotating about an axis which is parallel to the axis of rotation of the deflection roller, the turning roller with the uppermost point of its circumferential surface lying below the plane of the supporting surface and being out of contact with the latter while it is driven to rotate in the same direction as the deflection roller. Also, in this turning station, a draw-in wedge is formed between the turning roller and the deflection roller, in which draw-in wedge a transition roller is received, which rotates in the same direction as the turning roller and the deflection roller. In this context, it is advantageous to provide the circumferential surfaces of the turning roller and the transition roller with toothings, i.e. with toothed grooves. By such design of the turning roller, it is achieved that the fillets adhering to a smooth surface undergo less adhesion when in contact with the turning roller, so that it is safeguarded that the fillets can be released within an angle of rotation of the turning roller of between 90° to 180°. There is the possibility of a further contructional advantage if the double arrangement of the two inspecting devices is combined in one apparatus, which is achieved in that the conveyor belt is conducted over emitters lying in consecutive order with respect to the direction of movement of the conveyor belt and that the turning station is arranged in a position between these two light emitters. Also, it can be considered expedient to arrange an additional, preferably narrow conveyor belt running parallel to the inspection conveyor belt alongside the same, particularly on the side at which the inspecting person takes his place, and serving for the removal of fillets which have shown quality deficiencies.

BRIEF DESCRIPTION OF THE DRAWINGS

Other and further objects of the present invention will be apparent from the following description and claims and are illustrated in the accompanying drawings, which by way of illustration schematically show preferred embodiments of the present invention and the principles thereof and what now are considered to be the best modes contemplated for applying these principles. Other embodiments of the invention embodying the same or equivalent principles may be used and structural changes may be made as desired by those skilled in the art without departing from the present invention and the scope of the appended claims. In the drawings FIG. 1 shows a side-view of the apparatus according to the invention in axonometric representation and FIG. 2 shows a partial cross-section through a light emitter.

DETAILED DESCRIPTION OF THE PREFERRED EMBODIMENT

As shown in FIG. 1, an apparatus designed in accordance with the present invention comprises an endlessly rotating conveyor belt 1, which is arranged in a not-shown frame and driven in a suitable manner by an appropriate drive, also not shown for the sake of clearness. This conveyor belt 1 is manufactured from a material allowing light to pass therethrough at little absorption, and serves as a depositing and supporting surface 2 for fillets to be inspected. The guiding of the conveyor belt 1 is performed by a series of deflection rollers mounted in the afore-mentioned not-shown frame. The course and length of the conveyor belt 1 is determined by first and second deflection rollers referred to by numerals 3 and 4, respectively. While approximately the first third and the last third of the usable supporting surface 2 of the conveyor belt 1 extend in a mutual horizontal plane, the course of the conveyor belt 1 in the region of its middle third is below this plane. To this end, a further, third deflection roller 5 is provided between the first and second rollers 3, 4, which third deflection roller 5 guides the conveyor belt 1 to a tension roller 6. The latter then guides the conveyor belt 1 to a support roller 7 deflecting the belt 1 back again into the plane of the supporting surface 2. One light emitter 8 each is arranged between the first and third deflection rollers 3 and 5, on the one hand, and the support roller 7 and second deflection roller 4, on the other. Each light emitter 8 comprises a hermetically sealed, box-shaped housing 9 having a closing or sealing surface 10 being made from a transparent material. The housing 9 is arranged such that the sealing surface 10 lies essentially in the plane of the bottom surface of the conveyor belt 1. A number of light sources 11, which are preferably in the form of cold light emitting gas discharge lamps having tubular shape and being aligned in the conveying direction of the conveyor belt 1 are arranged in the housing 9. A screen 12 is associated to each of the light sources 11, these screens being mounted such that each light source 11 lies in a light shaft or gap 13 determined by and between two screens 12. The light shafts 13 are arranged at an inclination of approx. 45° with respect to the sealing surface 10. The arrangement of each light source 11 is such that these appear to be concealed by the screens 12 when a person is looking in a direction perpendicular to the sealing surface 10. When looking in the running direction of the conveyor belt 1, which direction is indicated by an arrow, a turning or reversing station 14 for the fillets is provided downstream of the deflection roller 5 and below the plane of the supporting surface 2. This turning station 14 comprises a turning or reversing roller 15 rotating about an axis parallel to that of deflection roller 5 and rotating in the same direction therewith. The circumferential surface of the turning roller 15 faces the surface of the conveyor belt 1 without contacting it but at a rather small distance. A wedge-shaped gap occurring between the turning roller 15 and the deflection roller 5 receives a transition roller 16 again rotating in the same direction as the turning roller 15 and the deflection roller 5 and is arranged such that there is just no contact with the conveyor belt 1 and the circumferential surface of the turning roller 15. The circumferential surfaces of the turning roller 15 and the transition roller 16 are provided with toothed grooves. Further deflection rollers or pulleys 18 and 19 are mounted on the axes of the first and second deflection rollers 3 and 4 on the operating side of the apparatus which is the side to the left-hand of the conveying direction indicated by the afore-mentioned arrow. The deflection pulleys 18 and 19 receive a conveyor 17 which rotates together with the conveyor belt 1. For an intermediate support of the conveyor 17 support pulleys 20 and 21 are provided, which are mounted on the axes of the deflection roller 5 and the support roller 7, respectively.

The function of the device is as follows:

A fillet deposited on the conveyor belt 1 e.g. from a skinning device at the end of a filletting line arrives in the region of the first light emitter 8 by a forward movement in the direction of the above-mentioned arrow. An inspecting person will sit opposite to said first light emitter 8 alongside the conveyor 17, i.e. on the operation side. For this inspecting person, the supporting surface 2 of the conveyor belt 1 appears to be only slightly illuminated in the region of the light emitter 8 according to the light absorption of the conveyor belt 1 caused by the material thereof. In the very moment the fillet enters the emitting area of the light emitter 8, the light rays, which have until then practically not been observable from the position of the inspecting person, enter into the fillet from below, which, due to the characteristic of its material to allow light to pass while being dispersed, appears to be illuminated internally. Since faulty areas and matter such as remainders of skin, blood patches, remainders of the belly skin, bones, parasites etc. have a higher light absorption, such places of deficiencies become visible as dark fields or spots. Thereafter, the fillet arrives in the area of the turning station 14 firstly on the transition roller 16 and then on the turning roller 15, whose circumferential surface has an adhesion effect on the fillet. This adhesion effects that the fillet is entrained over a certain angle of rotation and finally falls off again when the weight of the fillet surpasses the adhesion forces. Consequently, the fillet arrives back on the conveyor surface in a turned position, the conveyor belt 1 now performing the conveyance of the fillet to the area of the second light emitter 8. The function of the latter is the same one as that of the first light emitter.

Once a fillet deficiency has been discovered which is worthwhile to be objected to, the respective fillet may be taken off and put on the conveyor 17 which conveys it to a treatment or processing by trimming.

What is claimed is:

1. An apparatus for handling fillets of fish for the purpose of detecting fillet deficiencies in the form of at least one of processing faults and parasites (numatodes) by visual inspection, said apparatus comprising;
   a fillet supporting surface;
   said fillet supporting surface being light transparent and having a low light absorption;
   at least one light source below said fillet supporting surface;
   a screen below said fillet supporting surface;
   said screen including means to permit said at least one light source to illuminate an underside of said fillet supporting surface and to prevent direct passage of light therefrom to a position alongside said fillet supporting surface, such that looking at said apparatus from a position alongside said fillet supporting surface leave said at least one light source concealed from direct sight, whereby said fillets appear as bright objects against a darker background.

2. An apparatus as claimed in claim 1, wherein:
   said at least one light source include a hermetically sealed housing;
   said housing including a sealing surface; and
   said sealing surface being said light transparent fillet supporting surface.

3. An apparatus as claimed in claim 1, wherein said screen includes a first screen surface facing said at least one light source and a second screen surface facing said position, said first screen surface being light reflecting and said second screen surface being light absorbing whereby said supporting surface is seen against a dark background.

4. An apparatus as claimed in claim 2, wherein said screen includes a first screen surface facing said at least one light source and a second screen surface facing said position, said first screen surface being light reflecting and said second screen surface being light absorbing.

5. An apparatus as claimed in claim 1, wherein said at least one light source includes a cold light emitting light source.

6. An apparatus as claimed in claim 5 wherein said light source is tubular.

7. An apparatus as claimed in claim 2, wherein said at least one light source includes a cold light emitting light source.

8. An apparatus as claimed in claim 1 wherein said light source is tubular.

9. An apparatus as claimed in claim 3, wherein said at least one light source includes a cold light emitting light source.

10. An apparatus as claimed in claim 9 wherein said light source is tubular.

11. An apparatus as claimed in claim 4, wherein said at least one light source includes a cold light emitting light source.

12. An apparatus as claimed in claim 11 wherein said light source is tubular.

13. An apparatus as claimed in claim 1 wherein said fillet supporting surface includes an elongated surface having an elongate direction, and said at least one light source includes first and second light sources below said surface disposed in said elongate direction.

14. An apparatus as claimed in claim 2 wherein said hermetically sealed housing means includes first and second hermetically sealed housing means disposed in line to form an elongated surface.

15. An apparatus as claimed in claim 3, wherein said fillet supporting surface includes an elongated surface having an elongate direction, and said at least one light source includes first and second light sources below said surface disposed in said elongate direction.

16. An apparatus as claimed in claim 4 wherein said hermetically sealed housing means includes first and second hermetically sealed housing means disposed in line to form an elongated surface.

17. An apparatus as claimed in claim 1 wherein:
   conveying means for removing fillets showing quality deficiencies is disposed adjacent said position; and
   said conveying means runs parallel to said fillet supporting surface.

18. An apparatus as claimed in claim 2 wherein:
   conveying means for removing fillets showing quality deficiencies is disposed adjacent said position; and
   said conveying means runs parallel to said fillet supporting surface.

19. An apparatus as claimed in claim 3 wherein:
   conveying means for removing fillets showing quality deficiencies is disposed adjacent said position; and p1 said conveying means runs parallel to said fillet supporting surface.

* * * * *